United States Patent [19]

Abe et al.

[11] Patent Number: 4,847,260

[45] Date of Patent: Jul. 11, 1989

[54] COMPOSITION FOR PERCUTANEOUS ADMINISTRATION

[75] Inventors: Yoko Abe; Susumu Satoh; Mitsuhiko Hori; Naoko Yamanaka, all of Osaka, Japan

[73] Assignee: Nitto Denko Corporation, Tokyo, Japan

[21] Appl. No.: 113,352

[22] Filed: Oct. 26, 1987

Related U.S. Application Data

[63] Continuation of Ser. No. 798,515, Nov. 15, 1985, abandoned.

[30] Foreign Application Priority Data

Nov. 15, 1984 [JP] Japan ................................. 59-241456
Mar. 25, 1985 [JP] Japan ................................. 60-61687

[51] Int. Cl.$^4$ ...................... A61K 31/40; A61K 31/40; A61K 31/44; A61K 31/135
[52] U.S. Cl. ..................................... 514/279; 514/305; 514/356; 514/418; 514/652
[58] Field of Search ............... 514/356, 279, 305, 418, 514/652

[56] References Cited

U.S. PATENT DOCUMENTS 2,431,558 12/1947 Huber ................................. 514/356

OTHER PUBLICATIONS

Chem. Abst., vol. 66-103779c (1967) vol. 82-68706h (1975).

Primary Examiner—Stanley J. Friedman
Attorney, Agent, or Firm—Sughrue, Mion, Zinn, Macpeak & Seas

[57] ABSTRACT

A composition for percutaneous administration containing a nicotinic ester represented by formula (I)

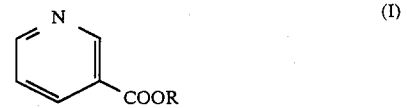

or an isonicotinic ester represented by formula (II)

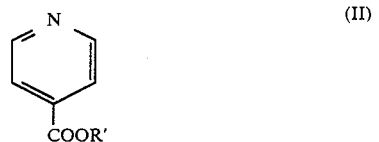

wherein R and R' each represents an alkyl group having 5 or more carbon atoms, with or without a specific polar compound. The composition improves percutaneous absorption of an active ingredient.

18 Claims, No Drawings

COMPOSITION FOR PERCUTANEOUS ADMINISTRATION

This is a continuation of application Ser. No. 798,515, filed Nov. 15, 1985, now abandoned.

FIELD OF THE INVENTION

This invention relates to a composition for percutaneous administration which can improve percutaneous absorption of an active ingredient and to a method of accelerating percutaneous absorption of an active ingredient.

BACKGROUND OF THE INVENTION

Percutaneous administration of drugs has been intended to produce topical effects of the skin or subcutaneous tissues beneath the skin, such as sterilization, disinfection, analgesia, antipruritus, antiinflammation, and the like, while systemic effects have been expected by oral administration or injection.

Oral administration has problems in that the absorbed drug is susceptible to first-order metabolism in the liver and that the concentration of the drug in the body should temporarily be higher than necessary in order to obtain long-lasting effect. Further, oral administration of some drugs like indomethacin causes gastrointestinal side effects. On the other hand, administration through injection, though advantageous for obtaining rapid absorption, requires specialists, such as physicians.

In order to overcome the above-described problems, there have recently been proposed methods for obtaining systemic effects through percutaneous administration. Percutaneous administration of drugs has various merits, such as that: the release of the active ingredient can easily be sustained; the concentrations of the active ingredient in the body are controllable; the drug enters from the skin directly into the blood flow, and is not, therefore, susceptible to first-order metabolism in the liver; and the like.

However, since the skin normally possesses a barrier function to prevent entrance of foreign matter into the interior of the body, the purpose of percutaneous administration has traditionally been limited to topical effects. Hence, when drugs are percutaneously administered aiming at systemic effects, it is required to use a percutaneous absorption-accelerating agent. In recent years, various absorption-accelerating agents have been proposed. For example, U.S. Pat. No. 3,551,554 discloses dimethyl sulfoxide, and, in addition, dimethylacetamide, dimethylformamide, methyldecyl sulfoxide, etc.

Additional examples of absorption-accelerating agents are ethyl alcohol, isopropyl alcohol or isopropyl palmitate in combination with a lower alkylamide, e.g., dimethylacetamide as disclosed in U.S. Pat. No. 3,472,431; combinations of 2-pyrrolidone and appropriate oils or esters of straight chain fatty acids and alcohols as disclosed in U.S. Pat. No. 4,017,641; and the like. However, these known agents are still unsatisfactory in terms of effects, safety, and feeling of use.

SUMMARY OF THE INVENTION

Accordingly, an object of this invention is to provide a composition for percutaneous administration which can increase percutaneous permeability and percutaneous absorbability of active ingredients.

Another object of this invention is to provide a method for increasing percutaneous permeability and percutaneous absorbability of active ingredients.

The present inventors have conducted extensive and intensive investigations in the light of the above-described circumstances, and, as a result, it has now been found that specific nicotinic esters or isonicotinic esters hereinafter described are effective to increase percutaneous permeability and absorbability of drugs and that these effects can further be ensured by a combined use of these esters with specific polar compounds.

That is, present invention relates to a composition for percutaneous administration containing a nicotinic ester represented by formula (I)

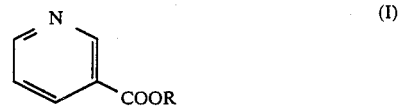

or an isonicotinic ester represented by formula (II)

where R and R' each represents an alkyl group having 5 or more carbon atoms.

Preferably, the composition contains a polar compound selected from the group consisting of lower alcohols, glycerin, glycerin esters, thioglycerols, lactic acid, lactic esters, cyclic urea compounds represented by the formula (III)

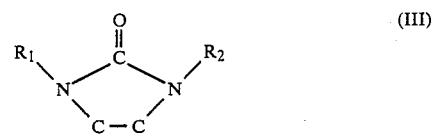

wherein $R_1$ and $R_2$ each represents a hydrogen atom or a lower alkyl group, amide compounds represented by formula (IV)

wherein $R_3$, $R_4$ and $R_5$ each represents a hydrogen atom or a lower alkyl group, alkylene glycols, monoalkyl ethers of mono- or diethylene glycol, lactones, urea compounds represented by formula (VI)

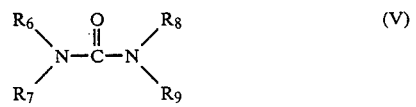

wherein $R_6$, $R_7$, $R_8$ and $R_9$ each represents a lower alkyl group, a nitro group, or an acyl group having 1 or 2 carbon atoms, and lactam compounds represented by formula (IV)

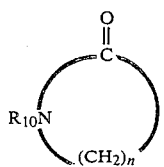

(VI)

wherein $R_{10}$ represents a hydrogen atom or a lower alkyl group, and n represents an integer of from 3 to 5.

The present invention further relates to a method for increasing percutaneous permeability and percutaneous absorbability of an active ingredient, which comprises percutaneously administering an active ingredient in the presence of a nicotinic ester of formula (I) or an isonicotinic ester of formula (II), and preferably in the copresence of the above described polar compound.

DETAILED DESCRIPTION OF THE INVENTION

In the above-described formula (I), the alkyl group as represented by R is a saturated or unsaturated, acyclic or cyclic alkyl group having 5 or more carbon atoms, and preferably from 6 to 24 carbon atoms. More specifically, the saturated alkyl group preferably contains from 5 to 20 carbon atoms and includes straight chain groups, e.g., an n-pentyl group, an n-hexyl group, and n-heptyl group, an n-octyl group, an n-nonyl group, an n-decyl group, an n-undecyl group, an n-dodecyl group, an n-tetradecyl group, an n-hexadecyl group, an n-octadecyl group, an n-eicosyl group, etc.; and branched chain alkyl groups, e.g., a 2-methylhexyl group, a 2-ethylhexyl group, a 3,7-dimethyloctyl group, a 2-hexyldecyl group, a 2-octyldodecyl group, a 2,4,4-trimethyl-1-pentyl group, a 1-methyloctyl group, etc. The unsaturated alkyl group preferably contains from 6 to 24 carbon atoms and includes a cis-3-hexenyl group, an oleyl group, a linoleyl group, etc. The cyclic alkyl group preferably has a total carbon atom number of from 6 to 12. Examples of the cyclic alkyl group are a 2-cyclohexylethyl group, a cycloheptyl group, a cyclohexylmethyl group, a ciclooctyl group, a 4-cyclohexylbutyl group, a 3-cyclopentylpropyl group, a 5-methyl-2-isopropylcyclohexyl group, etc. The cyclic moiety of these cyclic alkyl groups preferably contains from 6 to 8 carbon atoms, i.e., to form a 6- to 8-membered ring.

In formula (II), the alkyl group as represented by R' is the same as described for R in formula (I).

The polar compounds which can be preferably used in combination with the nicotinic ester (I) or isonicotinic ester (II) will be described below in detail.

The term "lower alkyl group" as used in formulae (III) to (VI) means an alkyl group having from 1 to 4 carbon atoms. Examples of the lower alkyl group are a methyl group, an ethyl group, an n-propyl group, an isopropyl group, an n-butyl group, an isobutyl group, etc.

The lower alcohols preferably include monohydric alcohols having from 1 to 6 carbon atoms. Specific examples of such alcohols include methyl alcohol, ethyl alcohol, n-propyl alcohol, isopropyl alcohol, n-butyl alcohol, isobutyl alcohol, sec-butyl alcohol, t-butyl alcohol, n-amyl alcohol, isoamyl alcohol, n-hexyl alcohol, cis-3-hexenol, etc.

The glycerin esters may be any of mono-, di-, and triesters. The acid component in the esters preferably includes fatty acids having from 2 to 6 carbon atoms, inter alia, acetic acid. Specific examples of these glycerin esters are glycerin monoacetate, glycerin diacetate, etc.

The thioglycerol may be any of mono-, di-, and triglycerols, and specifically includes α-monothioglycerol.

The lactic esters preferably have an aliphatic monohydric alcohol moiety containing from 1 to 4 carbon atoms. Specific examples of such esters include methyl lactate, ethyl lactate, butyl lactate, etc.

In formula (III), the lower alkyl group as represented to $R_1$ or $R_2$ preferably contains from 1 to 3 carbon atoms, including a methyl group, an ethyl group, an n-propyl group, an isopropyl group, etc. Specific examples of the cyclic urea compounds (III) and N,N'-dimethylethyleneurea, ethyleneurea, N,N'-diethylethyleneurea, etc.

In formula (IV), the lower alkyl group as represented by $R_3$, $R_4$ or $R_5$ preferably contains from 1 to 3 carbon atoms, including a methyl group, an ethyl group, an n-propyl group, an isopropyl group, etc. Specific examples of the amide compound (IV) are formamide, N-methylformamide, N,N-dimethylformamide, N,N-diethylformamide, acetamide, N-methylacetamide, N,N-dimethylacetamide, N,N-diethylacetamide, propionamide, N-methylpropionamide, N,N-dimethylpropionamide, N,N-diethylpropionamide, etc.

The alkylene glycols preferably contain an alkylene moiety of from 2 to 8 carbon atoms. Specific examples of such alkylene glycols are ethylene glycol, 1,3-propanediol, 1,2-propanediol, butanediol, pentanediol, 2-methyl-2,4-pentanediol, 2-ethyl-1,3-hexanediol, etc.

The monoalkyl ethers of mono- or diethylene glycol preferably contain an alkyl moiety of 1 to 2 carbon atoms. Specific examples include ethylene glycol monomethyl ether, ethylene glycol monoethyl ether, etc.

The lactones preferably have a 4- or 5-membered ring and specifically includes propiolactone, butyrolactone, etc.

In formula (V), the lower alkyl group as represented by $R_6$, $R_7$, $R_8$ or $R_9$ preferably contains from 1 to 4 carbon atoms, including a methyl group, an ethyl group, an n-propyl group, an isopropyl group, an n-butyl group, etc. Specific examples of the urea compound (V) include 1,1-dimethylurea, 1,3-dimethylurea, 1,1-diethylurea, 1,3-diethylurea, 1,1,3,3-tetramethylurea, etc.

In formula (VI), the lower alkyl group as represented by $R_{10}$ preferably contains from 1 to 3 carbon atoms, including a methyl group, an ethyl group, an n-propyl group, an isopropyl group, etc. Specific examples of the lactam compounds (VI) include 2-pyrrolidone, N-methylpyrrolidone, N-methylpiperidone, N-methylcaprolactam, etc.

When the nicotinic ester (I) or isonicotinic ester (II) is used in combination with at least one of the above-described polar compounds, the nicotinic ester or isonicotinic ester is preferably used in a proportion of from 0.5 to 70%, preferably 1.0 to 25%, by weight to a total amount of the nicotinic ester or isonicotinic ester and the polar compound or compounds.

The composition for percutaneous administration according to the present invention increases percutaneous permeability and percutaneous absorbability of an active ingredient. Therefore, the purposed effects can be produced by percutaneously administering the active ingredient in the presence of this composition. In a preferred embodiment of this invention, the active ingredient is beforehand incorporated in the composition of this invention to prepare a medical composition for external use.

The active ingredient to be incorporated in the composition for percutaneous administration according to the present invention is not particularly limited as long as it may be administered percutaneously. In contrast to cases where a drug is administered for topical purposes, use of the composition of the present invention aims at penetration of the drug deep into the interior of the body. In the cases where systemic effects are expected, the composition of the present invention helps the active ingredient to rapidly pass into the blood.

Active ingredients for topical use include topical anesthetics, e.g., procaine hydrochloride, tetracaine hydrochloride, dibucaine hydrochloride, lidocaine, lidocaine hydrochloride, piperocaine acetate, etc.; antihistaminics, e.g., diphenhydramine hydrochloride, chlorophenylamine maleate, bromophenylamine maleate, diphenylimidazole, clemizole hydrochloride, etc.; antibiotics, e.g., lincomycin, penicillin G, erythromycin, tetracycline hydrochloride, clindamycin, kanamycin, oxytetracycline, chloramphenicol, fradiomycin, nystatin, gramicidin hydrochloride, bacitracin, etc.; antifungals, e.g., griseofulvin, N-methyl-N-(3-tolyl)-thiocarbamic acid-2-naphthyl ester, diametazole hydrochloride, aureo thricin, trichomycin, pyrrolnitrin, 5-fluorocytosine, etc.; and the like.

Active ingredients for systemic use include benzodiazepins, e.g., diazepam, nitrazepam, flunitrazepam, lorazepam, prazepam, fludiazepam, clonazepam, etc.; diuretics, such as thiazides, e.g., bendroflumethiazide, polythiazide, methyclothiazide, trichlormethiazide, cyclopenthiazide, benzylhydrochlorothiazide, hydrochlorothiazide, bumetanide, etc.; hypotensives, e.g., clonidine, etc.; antihistaminics, such as aminoethers, e.g., diphenhydramine, carbinozamine, diphenylpyraline, etc.; ethylenediamines, e.g., phenbenzamine, etc.; monoamines, e.g., chlorpheniramine, etc.; non-steroid type antiinflammatory agents, e.g., indomethacin, ibuprofen, ibufenac, alclofenac, diclofenac, mefanic acid, flurbiprofen, flufenamic acid, ketoprofen, etc.; sodium salicylate, anticancer agents, e.g.; 5-fluorouracil, 1-(2-tetrahydrofuryl)-5-fluorouracil, cytarabine, Broxuridine, etc.; steroid type antiinflammatory agents, e.g., cortisone, hydrocorticone, prednisolone, triamcinolone, dexamethasone, betamethasone, etc.; antiepileptics, e.g., ethosuximide, etc.; antiarrhythmics, e.g., ajmaline, prajmaline, pindolol, propranolol, quinidine, etc.; psychoneurotropic agents, e.g., haloperidol, moperone, etc., scopolamines, e.g., methyl scopolamine, butyl scopolamine, etc., metoclopramide hydrochloride, chloropromazine, atropines, e.g., methylatropine bromide, methylanisotropine bromide, etc.; vasodilators, e.g., isosorbide dinitrate, nitroglycerin, pentaerythritol tetranitrate, propanyl nitrate, dipyridamole, etc.; antibiotics, such as tetracyclines, e.g., tetracycline, oxytetracycline, metacycline, doxycycline, minocycline, etc., chlorophenicols, erythromycines, etc.; and the like.

The amount of the active ingredient to be incorporated in the composition of the present invention can be appropriately determined depending on the kind of drug, body weight, and symptoms of patients and the like, as long as the desired pharaceutical effects can be manifested. In general, the active ingredient is preferably used in a amount of from 0.01 to 20% by weight, and more preferably from 0.2 to 10% by weight, based on the total amount of the nicotinic ester (I) or isonicotinic ester (II) and the polar compound. It should be noted, however, that the amounts of the active ingredient to be incorporated are not limited to the above-recited range, since the amount of the active ingredient to be applied can be controlled by increasing or decreasing the surface area to which the medical composition containing the active ingredient is applied.

The above-described medical composition in accordance with the present invention may further be mixed with conventional pharmaceutically acceptable additives and can be formulated into various dosage forms for external use, such as ointments, plasters, lotions, adhesive tapes, impregnations, gels, etc. The impregnations are prepared by absorbing the medical composition to an appropriate adsorbent, such as gauze, filter paper, porous membrane, etc., and are generally applied to the skin with an aid of adhesive tape. The gels are prepared by gelling the medical composition with, for example, dibenzolidene sorbitol (e.g., "Gelol R", trademark for a product manufactured by New Japan Chemical Co., Ltd.), and spreading the jelly on a support. Bases for the adhesive tapes are known per se and include acrylic copolymers, polyvinyl ether compounds, rubbery adhesive mixtures, and the like. Other dosage forms for external use can be prepared according to a known manner.

The present invention will now be illustrated in greater detail with reference to the following Preparation Examples, Formulation Examples and Test Examples, but it should be understood that these examples are not limiting the present invention. In these examples, all the percents are by weight unless otherwise indicated.

PREPARATION EXAMPLE 1

Preparation of n-Dodecyl Nicotinate $$[(I): R=(CH_2)_{11}CH_3]$$

In 100 ml of hexamethylphosphoramide was dissolved 4.9 g (0.04 mol) of nicotinic acid, and a 25% aqueous solution of sodium hydroxide (0.06 mol) was added thereto, followed by stirring using a magnetic stirrer at room temperature for 1 hour. To the mixture was further added 29.8 g (0.12 mol) of lauryl bromide, and the stirring was continued for an additional 24 hours. The reaction mixture was added to 200 ml of a 5% aqueous solution of hydrochloric acid and extracted with diethyl ether. The extract was washed with water, dried over sodium sulfate and distilled to remove the solvent. The residue was purified by column chromatography (Wakogel C-300, benzene:ethyl acetate=6:1 v/v) and recrystallized from methyl alcohol at 1° C. to obtain 9 g of n-dodecyl nicotinate as a colorless liquid in a yield of 77%, based on the nicotinic acid.

PREPARATION EXAMPLES 2 TO 5

Preparation of Nicotinic Esters (I)

Nicotinic esters having the following ester groups were prepared in the same manner as described in Example 1.

| Example No. | Ester Group (R) | Nicotinic Ester (I) |
| --- | --- | --- |
| 2 | $-(CH_2)_9CH_3$ | n-Decyl nicotinate |
| 3 | $-(CH_2)_{17}CH_3$ | n-Octadecyl nicotinate |
| 4 | $-(CH_2)_{15}CH_3$ | n-Cetyl nicotinate |

-continued

| Example No. | Ester Group (R) | Nicotinic Ester (I) |
|---|---|---|
| 5 | —(CH$_2$)$_7$CH$_3$ | n-Octyl nicotinate |

PREPARATION EXAMPLE 6

Preparation of 2-Ethylhexyl Nicotinate

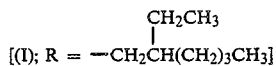

[(I); R = —CH$_2$CH(CH$_2$)$_3$CH$_3$]

A mixture of 10 g of nicotinic acid (0.08 mol), 25 g of thionyl chloride (0.21 mol), 1.5 ml of dimethylformamide and 200 ml of benzene was refluxed in an eggplant type flask for 3 hours. The solvent was removed by distillation. To the residue were added 20.8 g (0.16 mol) of 2-ethylhexyl alcohol and benzene, and the mixture was refluxed for 4 hours. The reaction mixture was poured into a saturated aqueous solution of sodium bicarbonate. The benzene layer was separated, washed successively with a saturated sodium bicarbonate aqueous solution, water and a saturated sodium chloride aqueous solution, dried over sodium sulfate and distilled to remove the solvent. The residue was purified by distillation under reduced pressure and column chromatography to obtain 9.1 g (70%) of 2-ethylhexyl nicotinate.

PREPARATION EXAMPLES 7 TO 14

Preparation of Nicotinic Esters (I)

Nicotinic esters having the following ester groups were prepared in the same manner as described in Example 6.

| Example No. | Ester Group (R) | Nicotinic Ester |
|---|---|---|
| 7 | —CH$_2$CH$_2$CH(CH$_3$)CH$_2$CH$_2$CH$_2$CH(CH$_3$)$_2$ | 3,7-Dimethyloctyl nicotinate |
| 8 | —CH$_2$CH(CH$_2$)$_7$CH$_3$<br>       \|<br>    (CH$_2$)$_5$CH$_3$ | 2-Hexyldecyl nicotinate |
| 9 | —CH$_2$CH$_2$CH=CHCH$_2$CH$_3$ | cis-3-Hexenyl nicotinate |
| 10 | —CH$_2$(CH$_2$)$_7$CH=CH(CH$_2$)$_7$CH$_3$ | Oleyl nicotinate |
| 11 | —CH$_2$CH=C(CH$_3$)(CH$_2$)$_2$CH=C(CH$_3$)$_2$ | Geranyl nicotinate |
| 12 | —CH$_2$CH$_2$—⬡ | 2-Cyclohexylethyl nicotinate |
| 13 | —CH$_2$(CH$_2$)$_3$—⬡ | 4-Cyclohexylbutyl nicotinate |
| 14 | (menthyl group) | Menthyl nicotinate |

PREPARATION EXAMPLE 15

Preparation of n-Decyl Isonicotinate

[(II); R' = —(CH$_2$)$_9$CH$_3$]

In 100 ml of hexamethylphosphoramide was dissolved 4.9 g (0.04 mol) of isonicotinic acid, and a 25% aqueous solution of sodium hydroxide (0.06 mol) was added to the solution, followed by stirring with a magnetic stirrer at room temperature for 1 hour. To the mixture was then added 26.5 g (0.12 mol) of decyl bromide, and the mixture was stirred for an additional 24 hours. The reaction mixture was added to 200 ml of a 5% aqueous solution of hydrochloric acid and extracted with diethyl ether. The extract was washed with water, dried over sodium sulfate and distilled to remove the solvent. Residual oil was purified by column chromatography under the following conditions. Silica gel (210 g) (Wakogel C-200, benzene:ethyl acetate=6:1 v/v). Purification of the residue by column chromatography yielded 6.7 g (63.7% based on isonicotinic acid) of n-decyl isonicotinate.

PREPARATION EXAMPLES 16 TO 20

Preparation of Isonicotinic Esters (II)

Isonicotinic esters having the following ester groups were prepared in the same manner as described in Example 15.

| Example No. | Ester Group (R') | Isonicotinic Ester |
|---|---|---|
| 16 | —(CH$_2$)$_5$CH$_3$ | n-Hexyl isonicotinate |
| 17 | —(CH$_2$)$_{11}$CH$_3$ | n-Dodecyl isonicotinate |
| 18 | —(CH$_2$)$_{17}$CH$_3$ | n-Octadecyl isonicotinate |
| 19 | —CH$_2$CH(CH$_2$)$_3$CH$_3$<br>       \|<br>    C$_2$H$_5$ | 2-Ethylhexyl isonicotinate |

-continued

| Example No. | Ester Group (R') | Isonicotinic Ester |
|---|---|---|
| 20 | —CH₂(CH₂)₃—⟨ ⟩ | 4-Cyclohexylbutyl isonicotinate |

FORMULATION EXAMPLES 1 TO 30

Basic Formulation:
(1) Active ingredient: 1% by weight
(2) Polar compound: 74% by weight
(3) Nicotinic ester (I): 25% by weight A basic formulation was prepared by mixing the components (2) and (3) indicated in Table 1 and then dissolving the component (1) indicated in Table 1 therein.

Control Formulation:
(1) Active ingredient: 1% by weight
(2) Dimethyl sulfoxide: 99% by weight The component (1) was dissolved in the component (2) to prepare a control formulation.

COMPARATIVE FORMULATION EXAMPLES 1 TO 5

(1) Active ingredient: 1% by weight
(2) Polar compound: 99% by weight

The component (1) shown in Table 2 was dissolved the component (2) shown in Table 2 to prepare a comparative formulation.

FORMULATION EXAMPLES 31 TO 38

(1) Active ingredient: 1% by weight
(2) Nicotinic Ester (I): 99% by weight

The component (1) shown in Table 3 was dissolved in the component (2) shown in Table 3.

FORMULATION EXAMPLES 39 TO 64

(1) Active ingredient: 1% by weight
(2) Nicotinic Ester (I): 10% by weight
(3) Polar compound: 89% by weight Formulations were prepared in the same manner as in Formulation Example 1, using the components (1) to (3) shown in Table 4.

TEST EXAMPLE 1

Each of the compositions prepared in Formulation Examples 1 to 64 and Comparative Formulation Examples 1 to 5 and Control Formulation was evaluated for percutaneous permeability of the active ingredient according to the following test method.

The skin cut from the abdomen of a rat was fixed to a glass-made permeation cell in such a manner that the surface side of the rat skin contacted the test composition and the back side thereof contacted physiological saline. The active ingredient having permeated into physiological saline through the skin was quantitatively determined by high performance liquid chromatography. The test was conducted in a sealed container.

The results obtained are set forth in Tables 1, 2, 3, and 4. In these tables, the Q values are obtained from the equation;

$$Q = \frac{C}{D}$$

wherein C represents the amount of the active ingredient permeated in the Example or Comparative Example, and D represents the active ingredient permeated in the Control Formulation.

TABLE 1

| Example No. | Active Ingredient | Polar Compound | Nicotinic Ester (I) | Q Value |
|---|---|---|---|---|
| 1 | propranolol hydrochloride | N—methylpyrrolidone | n-heptyl nicotinate | 6.5 |
| 2 | propranolol hydrochloride | N,N—dimethylacetamide | n-octyl nicotinate | 10.2 |
| 3 | propranolol hydrochloride | N,N'—dimethylethyleneurea | n-dodecyl nicotinate | 11.4 |
| 4 | propranolol hydrochloride | propylene glycol | 2-methylhexyl nicotinate | 2.2 |
| 5 | propranolol hydrochloride | ethanol | oleyl nicotinate | 5.7 |
| 6 | sodium salicylate | N—methylpyrrolidone | n-octyl nicotinate | 17.7 |
| 7 | sodium salicylate | N,N—dimethylacetamide | n-decyl nicotinate | 21.1 |
| 8 | sodium salicylate | N,N'—dimethylethyleneurea | 3,7-dimethyloctyl nicotinate | 29.3 |
| 9 | sodium salicylate | propylene glycol | 2-ethylhexyl nicotinate | 16.4 |
| 10 | sodium salicylate | ethanol | 2-cyclohexylethyl nicotinate | 20.3 |
| 11 | indomethacin | N—methylpyrrolidone | cis-3-hexenyl nicotinate | 6.4 |
| 12 | indomethacin | N,N—dimethylacetamide | n-decyl nicotinate | 14.1 |
| 13 | indomethacin | N,N'—dimethylethyleneurea | n-heptyl nicotinate | 7.3 |
| 14 | indomethacin | propylene glycol | n-2-methylhexyl nicotinate | 3.5 |
| 15 | indomethacin | ethanol | n-dodecyl nicotinate | 8.7 |
| 16 | methoclopramide hydrochloride | N—methylpyrrolidone | 2-ethylhexyl nicotinate | 11.7 |
| 17 | methoclopramide hydrochloride | N,N—dimethylacetamide | oleyl nicotinate | 25.2 |
| 18 | methoclopramide hydrochloride | N,N'—dimethylethyleneurea | cis-3-hexenyl nicotinate | 15.5 |
| 19 | methoclopramide hydrochloride | propylene glycol | n-octyl nicotinate | 4.8 |
| 20 | methoclopramide hydrochloride | ethanol | n-decyl nicotinate | 17.3 |
| 21 | diazepam | N—methylpyrrolidone | 2-cyclohexyl nicotinate | 2.5 |
| 22 | diazepam | N,N—dimethylacetamide | 2-methylhexyl nicotinate | 6.3 |

TABLE 1-continued

| Example No. | Active Ingredient | Polar Compound | Nicotinic Ester (I) | Q Value |
|---|---|---|---|---|
| 23 | diazepam | N,N'—dimethylethyleneurea | n-octyl nicotinate | 7.1 |
| 24 | diazepam | propylene glycol | n-dodecyl nicotinate | 2.9 |
| 25 | diazepam | ethanol | 3,7-dimethyloctyl nicotinate | 3.4 |
| 26 | theophylline | N—methylpyrrolidone | n-decyl nicotinate | 45.8 |
| 27 | theophylline | N,N—dimethylacetamide | 2-cyclohexylethyl nicotinate | 13.7 |
| 28 | theophylline | N,N'—dimethylethyleneurea | oleyl nicotinate | 36.1 |
| 29 | theophylline | propylene glycol | n-heptyl nicotinate | 22.7 |
| 30 | theophylline | ethanol | n-octyl nicotinate | 28.3 |

TABLE 2

| Comparative Example No. | Active Ingredient | Polar Compound | Q Value |
|---|---|---|---|
| 1 | propranolol hydrochloride | N—methylpyrrolidone | 0.74 |
| 2 | sodium salicylate | N,N'—dimethylethyleneurea | 0.33 |
| 3 | theophylline | N,N—dimethylacetamide | 0.52 |
| 4 | diazepam | propylene glycol | 0.05 |
| 5 | metoclopramide hydrochloride | ethanol | 0.54 |

TABLE 3

| Example No. | Active Ingredient | Nicotinic Ester (I) | Q Value |
|---|---|---|---|
| 31 | propranolol hydrochloride | n-hexyl nicotinate | 2.3 |
| 32 | propranolol hydrochloride | n-octyl nicotinate | 13.5 |
| 33 | propranolol hydrochloride | n-decyl nicotinate | 8.8 |
| 34 | propranolol hydrochloride | n-dodecyl nicotinate | 5.7 |
| 35 | metoclopramide hydrochloride | n-hexyl nicotinate | 4.6 |
| 36 | metoclopramide hydrochloride | n-octyl nicotinate | 4.4 |
| 37 | metoclopramide hydrochloride | n-decyl nicotinate | 4.4 |
| 38 | metoclopramide hydrochloride | n-dodecyl nicotinate | 2.5 |

TABLE 4

| Example No. | Active Ingredient | Polar Compound | Nicotinic Ester (I) | Q Value |
|---|---|---|---|---|
| 39 | propranolol hydrochloride | propylene glycol | n-hexyl nicotinate | 15.7 |
| 40 | propranolol hydrochloride | N—methylpyrrolidone | n-hexyl nicotinate | 23.1 |
| 41 | propranolol hydrochloride | ethanol | n-hexyl nicotinate | 8.0 |
| 42 | propranolol hydrochloride | propylene glycol | n-octyl nicotinate | 20.4 |
| 43 | propranolol hydrochloride | N—methylpyrrolidone | n-octyl nicotinate | 21.9 |
| 44 | propranolol hydrochloride | ethanol | n-octyl nicotinate | 14.9 |
| 45 | propranolol hydrochloride | propylene glycol | n-decyl nicotinate | 17.2 |
| 46 | propranolol hydrochloride | N—methylpyrrolidone | n-decyl nicotinate | 21.9 |
| 47 | propranolol hydrochloride | ethanol | n-decyl nicotinate | 8.2 |
| 48 | propranolol hydrochloride | propylene glycol | n-dodecyl nicotinate | 16.0 |
| 49 | propranolol hydrochloride | N—methylpyrrolidone | n-dodecyl nicotinate | 19.7 |
| 50 | propranolol hydrochloride | ethanol | n-dodecyl nicotinate | 12.9 |
| 51 | diazepam | propylene glycol | n-hexyl nicotinate | 1.4 |
| 52 | diazepam | N—methylpyrrolidone | n-hexyl nicotinate | 2.0 |
| 53 | diazepam | propylene glycol | n-dodecyl nicotinate | 2.7 |
| 54 | diazepam | N—methylpyrrolidone | n-dodecyl nicotinate | 2.8 |
| 55 | diazepam | ethanol | n-dodecyl nicotinate | 1.9 |
| 56 | metoclopramide | propylene glycol | n-hexyl nicotinate | 15.7 |
| 57 | metoclopramide | N—methylpyrrolidone | n-hexyl nicotinate | 20.7 |
| 58 | metoclopramide | ethanol | n-hexyl nicotinate | 12.6 |
| 59 | metoclopramide | propylene glycol | n-dodecyl nicotinate | 8.5 |
| 60 | metoclopramide | N—methylpyrrolidone | n-dodecyl nicotinate | 16.1 |
| 61 | metoclopramide | ethanol | n-dodecyl nicotinate | 5.5 |
| 62 | indomethacin | propylene glycol | n-hexyl nicotinate | 1.7 |
| 63 | indomethacin | propylene glycol | n-dodecyl nicotinate | 2.6 |
| 64 | indomethacin | N—methylpyrrolidone | n-dodecyl nicotinate | 2.5 |

FORMULATION EXAMPLES 65 TO 94

Basic Formulation:
(1) Active ingredient: 1% by weight
(2) Polar compound: 89% by weight
(3) Isonicotinic Ester (II): 10% by weight A composition was prepared by mixing the components (2) and (3) shown in Table 5, and then dissolving the component (1) shown in Table 5 therein.

Control Formulation:
(1) Active ingredient: 1% by weight
(2) Dimethyl sulfoxide: 99% by weight A composition was prepared by dissolving the component (1) in the component (2).

COMPARATIVE FORMULATION EXAMPLES 6 TO 15

(1) Active ingredient: 1% by weight
(2) Polar compounds: 99% by weight

A composition was prepared by dissolving the component (1) shown in Table 6 in the component (2) shown in Table 6.

COMPARATIVE FORMULATION EXAMPLES 16 TO 26

(1) Active ingredient: 1% by weight
(2) Polar compound: 89% by weight
(3) Ethyl isonicotinate: 10% by weight A composition was prepared by mixing the components (2) and (3) shown in Table 7 and dissolving the component (1) shown in Table 7 therein.

COMPARATIVE FORMULATION EXAMPLES 27 TO 39

(1) Active ingredient: 1% by weight
(2) Polar compound: 89% by weight
(3) Butyl isonicotinate: 10% by weight A composition was prepared by mixing the components (2) and (3) shown in Table 8 and dissolving the component (1) shown in Table 8 therein.

TEST EXAMPLE 2

Each of the compositions prepared in Formulation Examples 65 to 94 and Comparative Formulation Examples 6 to 39 and Control Formulation was evaluated for percutaneous permeability of the active ingredient in the same manner as described in Test Example 1. The results obtained are shown in Table 5, 6, 7 and 8.

TABLE 5

| Example No. | Active Ingredient | Polar Compound | Isonicotinic Ester (II) | Q Value |
| --- | --- | --- | --- | --- |
| 65 | propranolol hydrochloride | N,N'—dimethylethyleneurea | n-dodecyl isonicotinate | 10.2 |
| 66 | propranolol hydrochloride | N—methylpyrrolidone | n-hexadecyl isonicotinate | 1.4 |
| 67 | propranolol hydrochloride | propylene glycol | n-hexyl isonicotinate | 7.9 |
| 68 | propranolol hydrochloride | ethanol | 2-ethylhexyl isonicotinate | 7.4 |
| 69 | propranolol hydrochloride | N,N—dimethylacetamide | n-octadecyl isonicotinate | 1.1 |
| 70 | propranolol hydrochloride | N,N—dimethylformamide | n-heptyl isonicotinate | 13.6 |
| 71 | metoclopramide hydrochloride | N,N'—dimethylethyleneurea | 4-cyclohexylbutyl isonicotinate | 1.4 |
| 72 | metoclopramide hydrochloride | N—methylpyrrolidone | n-heptyl isonicotinate | 17.0 |
| 73 | metoclopramide hydrochloride | propylene glycol | n-dodecyl isonicotinate | 14.5 |
| 74 | metoclopramide hydrochloride | ethanol | n-hexyl isonicotinate | 21.6 |
| 75 | metoclopramide hydrochloride | N,N—dimethylacetamide | n-octyl isonicotinate | 27.6 |
| 76 | metoclopramide hydrochloride | N,N—dimethylformamide | n-decyl isonicotinate | 35.5 |
| 77 | sodium salicylate | N,N'—dimethylethyleneurea | n-heptyl isonicotinate | 2.3 |
| 78 | sodium salicylate | N—methylpyrrolidone | n-octyl isonicotinate | 2.8 |
| 79 | sodium salicylate | propylene glycol | n-decyl isonicotinate | 1.8 |
| 80 | sodium salicylate | ethanol | 4-cyclohexylbutyl isonicotinate | 1.1 |
| 81 | sodium salicylate | N,N—dimethylacetamide | n-hexyl isonicotinate | 9.0 |
| 82 | sodium salicylate | N,N—dimethylformamide | 2-ethylhexyl isonicotinate | 2.9 |
| 83 | diazepam | N,N'—dimethylethyleneurea | n-decyl isonicotinate | 2.3 |
| 84 | diazepam | N—methylpyrrolidone | n-dodecyl isonicotinate | 2.4 |
| 85 | diazepam | propylene glycol | n-tetradecyl isonicotinate | 1.4 |
| 86 | diazepam | ethanol | n-hexadecyl isonicotinate | 1.2 |
| 87 | diazepam | N,N—dimethylacetamide | n-heptyl isonicotinate | 1.0 |
| 88 | diazepam | N,N—dimethylformamide | 2-ethylhexyl isonicotinate | 2.1 |
| 89 | indomethacin | N,N'—dimethylethyleneurea | n-hexyl isonicotinate | 1.9 |
| 90 | indomethacin | N—methylpyrrolidone | n-hexyl isonicotinate | 4.5 |
| 91 | indomethacin | propylene glycol | n-dodecyl isonicotinate | 12.2 |
| 92 | indomethacin | ethanol | 2-ethylhexyl isonicotinate | 3.2 |
| 93 | indomethacin | N,N—dimethylacetamide | n-octyl isonicotinate | 5.6 |
| 94 | indomethacin | N,N—dimethylformamide | n-tetradecyl isonicotinate | 11.1 |

TABLE 6

| Comparative Example No. | Active Ingredient | Polar Compound | Q Value |
|---|---|---|---|
| 6 | Propranolol hydrochloride | N,N'—Dimethyl-ethyleneurea | 0.29 |
| 7 | Propranolol hydrochloride | Propylene glycol | 0.41 |
| 8 | Metoclopramide hydrochloride | N—Methylpyrrolidone | 0.41 |
| 9 | Metoclopramide hydrochloride | N,N—Dimethylacetamide | 0.64 |
| 10 | Sodium salicylate | Propylene glycol | 0.004 |
| 11 | Sodium salicylate | N,N—Dimethylformamide | 0.25 |
| 12 | Diazepam | N—Methylpyrrolidone | 0.59 |
| 13 | Diazepam | Ethanol | 0.29 |
| 14 | Indomethacin | Propylene glycol | 0.07 |
| 15 | Indomethacin | Ethanol | 0.32 |

TABLE 7

| Comparative Example No. | Active Ingredient | Polar Compound | Q Value |
|---|---|---|---|
| 16 | Propranolol hydrochloride | N,N'—Dimethyl-ethyleneurea | 0.13 |
| 17 | Propranolol hydrochloride | N—Methylpyrrolidone | 0.24 |
| 18 | Propranolol hydrochloride | Propylene glycol | 0.05 |
| 19 | Propranolol hydrochloride | Ethanol | 0.84 |
| 20 | Propranolol hydrochloride | N,N—Dimethylacetamide | 0.26 |
| 21 | Propranolol hydrochloride | N,N—Dimethylformamide | 0.56 |
| 22 | Diazepam | N—Methylpyrrolidone | 0.44 |
| 23 | Diazepam | Propylene glycol | 0.04 |
| 24 | Diazepam | Ethanol | 0.66 |
| 25 | Diazepam | N,N—Dimethylacetamide | 0.84 |
| 26 | Diazepam | N,N—Dimethylformamide | 0.97 |

TABLE 8

| Comparative Example No. | Active Ingredient | Polar Compound | Q Value |
|---|---|---|---|
| 27 | Propranolol hydrochloride | Propylene glycol | 0.04 |
| 28 | Diazepam | N,N'—Dimethyl-ethyleneurea | 0.16 |
| 29 | Diazepam | Propylene glycol | 0.05 |
| 30 | Diazepam | Ethanol | 0.60 |
| 31 | Metoclopramide | N,N'—Dimethyl-ethyleneurea | 0.65 |
| 32 | Metoclopramide | Propylene glycol | 0.12 |
| 33 | Indomethacin | N,N'—Dimethyl-ethyleneurea | 0.15 |
| 34 | Indomethacin | N—Methylpyrrolidone | 0.26 |
| 35 | Indomethacin | Propylene glycol | 0.30 |
| 36 | Indomethacin | Ethanol | 0.16 |
| 37 | Indomethacin | N,N—Dimethylacetamide | 0.17 |
| 38 | Indomethacin | N,N—Dimethylformamide | 0.21 |
| 39 | Sodium salicylate | Propylene glycol | 0.04 |

While the invention has been described in detail and with reference to specific embodiments thereof, it will be apparent to one skilled in the art that various changes and modifications can be made therein without departing from the spirit and scope thereof.

What is claimed is:

1. A composition for percutaneous administration comprising an antiarrhythmic as an active ingredient in a physiologically effective amount for percutaneous administration and an amount of a nicotinic ester represented by formula (I)

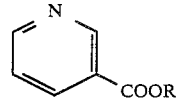

(I)

or an isonicotinic ester represented by formula (II)

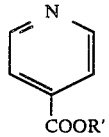

(II)

wherein R and R' each represents an alkyl group having 5 or more carbon atoms effective to increase the percutaneous permeability and absorbability through the skin of the antiarrhythmic.

2. A composition for percutaneous administration comprising a nicotinic ester represented by formula (I)

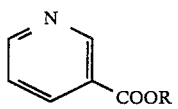

(I)

or an isonicotinic ester represented by formula (II)

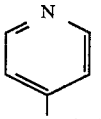

(II)

wherein R and R' each represents an alkyl group having 5 of more carbon atoms, an antiarrhythmic as an active ingredient and at least one polar compound selected from the group consisting of a lower alcohol, an alkylene glycol and a monoalkyl ether of mono- or diethylene glycol, wherein the nicotinic ester or isonicotinic ester is present in an amount of from 0.5 to 70% by weight and the antiarrhythmic is present in an amount of from 0.01 to 20% by weight both based on the total amount of the nicotinic ester or isonicotinic ester and the polar compound or compounds.

3. A composition as in claim 2, wherein the antiarrhythmic is used in an amount of from 0.2 to 10% by weight based on the total weight of the nicotinic ester (I) or isonicotinic ester (II) and the polar compound.

4. A composition as in claim 1, wherein R and R' each represents an alkyl group having from 6 to 24 carbon atoms.

5. A composition as in claim 2, wherein the lower alcohol contains from 1 to 6 carbon atoms.

6. The composition of claim 1 wherein said antiarrhythmic is selected from the group consisting of ajmaline, prajmaline, pindolol, propranolol and quinidine.

7. The composition of claim 1 wherein said antiarrhythmic is propranolol.

8. The composition of claim 2 wherein said antiarrhythmic is selected from the group consisting of ajmaline, prajmaline, pindolol, propranolol and quinidine.

9. The composition of claim 2 wherein said antiarrhythmic is propranolol.

10. A method for increasing percutaneous permeability and percutaneous absorbability of an antiarrhythmic as an active ingredient, which comprises the percutaneous administration of a composition comprising a nicotinic ester represented by formula (I)

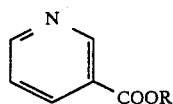
(I)

or an isonicotinic ester represented by formula (II)

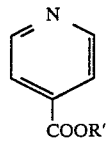
(II)

wherein R and R' each represents an alkyl group having 5 or more carbon atoms, and the active ingredient, wherein the antiarrhythmic is present in a physiologically effective amount for percutaneous administration and the nicotinic ester or isonicotinic ester is present in an amount effective to increase the percutaneous permeability and absorbability through the skin of the antiarrhythmic.

11. A method for increasing percutaneous permeability and percutaneous absorbability of an antirrhythmic as an active ingredient, which comprises the percutaneous administration of a composition comprising of a nicotinic ester represented by formula (I)

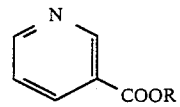
(I)

or an isonicotinic ester represented by formula (II)

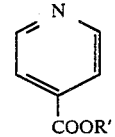
(II)

wherein R and R' each represents and alkyl group having 5 or more carbon atoms, an active ingredient and a polar compound, wherein the nicotinic ester or isonicotinic ester is present in an amount of from 0.5 to 70% by weight and the antiarrhythmic is present in an amount of from 0.01 to 20% by weight, both based on the total amount of the nicotinic ester or isonicotinic ester and the polar compound or compounds.

12. A method as in claim 10, wherein R and R' each represents an alkyl group having from 6 to 24 carbon atoms.

13. A method as in claim 11, wherein the antiarrhythmic is used in an amount of from 0.2 to 10% by weight based on the total weight of the nicotinic ester (I) or isonicotinic ester (II) and the polar compound.

14. A method as in claim 11, wherein the lower alcohol contains from 1 to 6 carbon atoms.

15. The method of claim 10 wherein said antiarrhythmic is ajmaline, prajmaline, pindolol, propranolol and quinidine.

16. The method of claim 10 wherein said antiarrhythmic is propranolol.

17. The method of claim 11 wherein said antiarrhythmic is selected from the group consisting of ajmaline, prajmaline, pindolol, propranolol and quinidine.

18. The method of claim 11 wherein said antiarrhythmic is propranolol.

* * * * *